United States Patent [19]

Kato et al.

[11] 4,429,035
[45] Jan. 31, 1984

[54] BLACK AND WHITE PHOTOGRAPHIC MATERIALS

[75] Inventors: Eiichi Kato; Nobutaka Ohki; Junkichi Ogawa, all of Kanagawa, Japan

[73] Assignee: Fuji Photo Film Co., Ltd., Kanagawa, Japan

[21] Appl. No.: 504,855

[22] Filed: Jun. 20, 1983

Related U.S. Application Data

[63] Continuation of Ser. No. 368,927, Apr. 16, 1982, abandoned.

[30] Foreign Application Priority Data

Apr. 17, 1981 [JP] Japan ............................ 56-58069

[51] Int. Cl.³ .............................................. G03C 7/16
[52] U.S. Cl. .................................... 430/402; 430/356; 430/565
[58] Field of Search ...................... 430/356, 402, 565

[56] References Cited

U.S. PATENT DOCUMENTS

| | | | |
|---|---|---|---|
| 3,650,762 | 3/1972 | Shiba et al. | 430/573 |
| 3,697,275 | 10/1972 | Hayakawa et al. | 430/270 |
| 3,756,818 | 9/1973 | Hayakawa et al. | 430/331 |
| 4,126,461 | 11/1978 | Pupo et al. | 430/402 |
| 4,387,158 | 6/1983 | Postle | 430/402 |

Primary Examiner—M. F. Downey
Attorney, Agent, or Firm—Sughrue, Mion, Zinn, Macpeak and Seas

[57] ABSTRACT

A black and white photographic material is disclosed. The material contains a black image-forming coupler shown by formula (I) or (II)

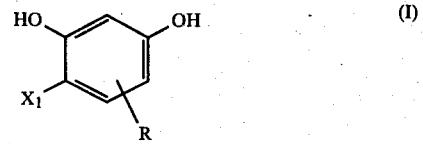

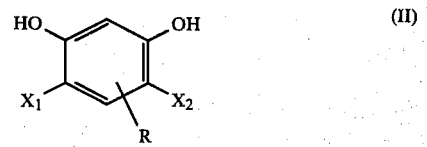

wherein R represents

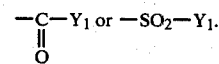

$Y_1$ represents a group which prevents the coupler from diffusing away from the layer containing it. Examples of such groups include an aliphatic group, an aryl group, an aralkyl group, or a heterocyclic group. $X_1$ and $X_2$ each represents a hydrogen atom or a coupling-off group capable of being released upon oxidative coupling reaction with a developing agent. The material is capable of producing an excellent black image by development after image exposure. In the photographic material, the amount of silver can be effectively reduced and the photographic material give black images even after bleaching the black image formed.

18 Claims, 1 Drawing Figure

BLACK AND WHITE PHOTOGRAPHIC MATERIALS

This application is a continuation of application Ser. No. 368,927 filed April 16, 1982 now abandoned.

BACKGROUND OF THE INVENTION

This invention relates to a silver halide photographic material containing a novel black and white image-forming coupler and a process of forming black and white photographic images using the photographic material. More particularly, the invention relates to a silver halide photographic material which can imagewise form a novel black dye in place of silver images, thereby the amount of silver in the photographic material is reduced, and further to a process of forming images using the foregoing silver halide photographic material.

In an ordinary process of forming black and white photographic images, a silver halide photographic material is imagewise exposed to form a latent image therein. The photographic material is then processed by an ordinary black and white developer containing an ordinary black and white developing agent such as, for example, hydroquinone, Metol, phenidone, etc. Metallic silver formed at the latent image portion is utilized as the black and white image.

At present the shortage of silver resources has become a serious problem. The tendency of at least partially substituting some materials for silver in black and white photographic images has been raised in the field of the art. One of these attempts is the replacement with a black dye.

Various processes have been proposed for the purpose. For example, the following processes are known: (1) forming a black dye image from 1,5-dihydroxynaphthalene and 2,5-dibromo-4-aminophenol as described in U.S. Pat. No. 1,939,231; (2) a process of forming a black image using a p-phenylenediamine derivative and phenol, naphthol, or an active methylene compound as described in U.S. Pat. No. 2,181,944; (3) a process of forming a black image using 3-aminopyrazolobenzimidazole as a developing agent and an active methylene compound as a coupler as described in West German Patent No. 1,158,836; (4) a process of forming a black image by color developing a mixture of couplers capable of forming yellow, magenta, and cyan dyes used usually in present color photography as described in British Pat. No. 492,518 and West German Patent No. 537,923; (5) a process of reducing the coating amount of silver by performing coloring development under the presence of color coupler and then fixing without removing silver to form a dye image and a silver image simultaneously as described in Japanese Patent Application (OPI) No. 37539/72 (the term "OPI" as used herein refers to a "published unexamined Japanese patent application"); (6) a process of forming a black image using an m-aminophenol derivative as a coupler as described in Japanese Patent Application (OPI) No. 52725/77; and (7) a process for forming a black image using a multifunctional coupler and a multifunctional developing agent as described in Japanese Patent Application (OPI) No. 57827/77.

However, when using these methods, a high image density is not obtained for the amount of coated silver and the materials for forming images are relatively expensive. Therefore, these methods have not yet been practically used.

In addition, Japanese Patent Application (OPI) No. 9924/79 describes a method of forming a black dye using a non-diffusible type resorcin coupler. However, this method is disadvantageous because a sufficiently neutral density, that is, a deep-black color image is not obtained by the coupler as described in the foregoing patent application. Furthermore, the amount of the dye formed per unit amount of coated silver is small, which shows the reducibility of the amount of coated silver is low.

SUMMARY OF THE INVENTION

An object of this invention is, therefore, to provide an image-forming material which can give the high maximum density of black image in spite of a reduced amount of silver in the silver halide photographic material.

Another object of this invention is to provide an image-forming material which can give a black image having almost no other color in spite of a reduced amount of silver in the silver halide photographic material.

Still another object of this invention is to provide a process of forming black images using the above described image-forming material.

These and other objects of this invention can be attained by using the black image-forming coupler shown by following general formulae (I) or (II)

wherein R represents wherein $Y_1$ represents a group for preventing the coupler from being diffused from the coated layer thereof, i.e., an aliphatic group, an aryl group, an aralkyl group, or a heterocyclic group and $X_1$ and $X_2$ each represents a hydrogen atom or a coupling-off group capable of being released by an oxidative coupling reaction with a developing agent.

DETAILED DESCRIPTION OF THE INVENTION

The characteristic feature of this invention involves the use of a black image-forming coupler shown by foregoing general formula (I) or (II). The black image-forming coupler used in this invention will now be explained in detail.

In formula (I) or (II), $Y_1$ shown by R in the formula shows practically an unsubstituted alkyl group or substituted alkyl group having 1 to 22 carbon atoms (e.g., methyl, ethyl, n-propyl, i-propyl, n-butyl, t-butyl, i-amyl, n-octyl, n-decyl, n-dodecyl, pentadecyl, 3-chloropropyl, 2-cyanoethyl, 2-ethoxyethyl, 2-n-butoxycarbonylethyl, etc.); an unsubstituted or substituted alkenyl group having 2 to 22 carbon atoms (e.g., vinyl, allyl, etc.); an unsubstituted or substituted aralkyl group having 7 to 22 carbon atoms (e.g., benzyl, phenethyl, 4-methylbenzyl, etc.); an unsubstituted or substituted aryl group having 6 to 22 carbon atoms (e.g., phenyl, 4-methylphenyl, 4-chlorophenyl, 2,4-dichlorophenyl, 4-n-decyloxyphenyl, 4-methoxyphenyl, 3-acetamidophenyl, 3-propylcarbamoylphenyl, 4-ethylcarbonylphenyl, 4-ethoxycarbonylphenyl, 3-methanesulfonylphenyl, 2-chloro-4-methoxyphenyl, 4-cyanophenyl, naphthyl, etc.); an unsubstituted or substituted cycloalkyl group having 5 to 22 carbon atoms (e.g., cyclopentyl, cyclohexyl, etc.); or an unsubstituted or substituted heterocyclic group having 5 to 22 carbon atoms (e.g., pyridyl, furyl, quinolyl, etc.).

$X_1$ and $X_2$ in formulae (I) and (II) each represents a hydrogen atom or a coupling-off group capable of being released upon oxidative coupling reaction with a developing agent and practical examples of the coupling-off group include a halogen atom (e.g., chlorine, bromine, etc.); an unsubstituted or substituted alkoxy group (e.g., ethoxy, n-dodecyloxy, methoxyethylcarbamoylmethoxy, carboxymethoxy, methylsulfonamidoethoxy, ethylsulfonylethoxy, etc.); an aryloxy group (e.g., phenyloxy, naphthyloxy, etc.); an alkylthio group (e.g., ethylthio, n-butylthio, n-decylthio, 3-chloropropylthio, etc.); an arylthio group (e.g., phenylthio, 4-methoxyphenylthio, 2,5-dihydroxy-3-di-n-butylcarbamoylphenyl, naphthylthio, etc.); an acyloxy group (e.g., acetoxy, tetradecanoyloxy, benzoyloxy, etc.); a sulfonyloxy group (e.g., methanesulfonyloxy, dodecanesulfonyloxy, etc.); an acylamino group (e.g., dichloroacetylamino, heptafluorobutyrylamino, etc.); a sulfonylamino group (e.g., methanesulfonylamino, dodecanesulfonylamino, benzenesulfonylamino, etc.); an alkyloxycarbonyloxy group (e.g., ethoxycarbonyloxy, benzyloxycarbonyloxy, etc.); an aryloxycarbonyloxy group (e.g., phenoxycarbonyloxy, etc.); and an imido group (e.g., succinimido, hydantoinyl, etc.).

In the foregoing formula (I), R may be substituted at the 2-position, 4-position or 5-position of the resorcin nucleus but from the viewpoint of giving excellent black color, it is preferred that R is substituted at the 2-position or 5-position.

Furthermore, in the coupler shown by formula (I) or (II) most preferably used in this invention, R is bonded at the 2-position of the resorcin nucleus.

In the image density of the black and white photographic image obtained by color developing the silver halide photographic material containing the above described coupler after image-exposure, more than 25% of the color density is created by the dye.

Typical examples of the couplers used in this invention are shown below but the invention is not limited to them.

(1)

(2)

(3)

(4)

(5)

(6)

(7)

(8)

(9)

-continued

(10)

(11)

(12)

(13)

(14)

(15)

(16)

(17)

(18)

-continued (19)

(20)

(21)

The coupler shown by formula (I) or (II) can be generally prepared from a dihydroxybenzoic acid or a compound shown by general formula (III), i.e., dihydroxybenzenesulfonic acid having protected hydroxy groups prepared by the method described in, for example, *J. Amer. Chem. Soc.*, 59, 2575 (1937) incorporated herein by reference to disclose how to make the compound of formula (I)

(III)

wherein R' represents a protective group which can be released by an acid, an alkali or a reduction reaction, such as an alkyl group (e.g., methyl, etc.), an aralkyl group (e.g., benzyl, etc.) or an acyl group (e.g., acetyl, benzoyl, methanesulfonyl, benzenesulfonyl, etc.) and Z represents a carboxy group or a sulfo group.

Practically, when R is $$-\underset{\underset{O}{\|}}{C}-Y_1,$$

the dihydroxy compound can be produced by a method of reacting the carbonyl compound obtained by the reaction of dimethoxybenzoic acid quinolinol ester and a Grignard reagent (see, for example, *Chem. Lett.*, 793 (1972) incorporated herein by reference) or the reaction of dimethoxybenzoic acid and an organolithium compound (see, for example, *Org. React.*, 18, 1, incorporated herein by reference) with hydrogen bromide, hydrogen iodide or boron tribromide; a method of subjecting an acyl compound obtained by reacting resorcinol-4,6-dicarboxylic acid ester and an acid chloride in the presence of a Lewis acid (e.g., anhydrous aluminum chloride, etc.) to an alkali hydrolysis-decarboxylation treatment (see, for example, *Hindustan Antibiot. Bull.*, 9 (1), 27 (1966) incorporated herein by reference and *Chem. Abst.*, 66, 11, 5388n (1967) incorporated herein by reference); or a method of acylating a cumarin derivative followed by decomposition (see, for example, *Org. Snth. Collect.*, Vol. 3, page 9281).

When R is —$SO_2$—$Y_1$, the dihydroxy compound is produced by a method of hydrolyzing (with, e.g., hydrogen bromide, boron tribromide, etc.) in an acid state a sulfonyl compound obtained by reacting resorcinol dimethyl ether and a sulfonyl chloride in the presence of a Lewis acid (see, e.g., *J. Chem. Soc.*, (1945), p. 14 (incorporated herein by reference)), a method of oxidizing a dimethoxybenzenealkyl sulfide obtained by the method described in *J. Am. Soc.*, 59, 2575 (1937), *Synthesis* (1975), p. 43, Academic Press, New York (using, for example, hydrogen peroxide, peracetic acid, etc., as the oxidizing agent) to form a sulfonyl compound and then hydrolyzing the sulfonyl compound as in the above case, a method of hydrolyzing the compound obtained by reacting a dimethoxybenzenesulfonyl chloride and a benzene derivative, or a method of reacting dimethoxybenzenesulfinic acid and an alkyl halide.

Practical examples of preparing the couplers used in this invention are explained by the following synthesis examples.

SYNTHESIS EXAMPLE 1

Synthesis of Compound (2):

In a 1 l three-neck flask was placed 26.5 g of 8-(2',6'-dimethoxybenzoyloxy)quinoline (melting point 120°–121° C.). After dissolving the quinoline in 300 ml of dessicated tetrahydrofuran, the solutiom was stirred under ice-cooling. To the solution was added dropwise over a period of 30 minutes 150 ml of a dessicated diethyl ether solution of decylmagnesium bromide prepared from 33 g of decyl bromide by an ordinary manner. Thereafter, the mixture was stirred for 1 hour under ice-cooling and then for 1 hour at room temperature to precipitate a magnesium complex of 8-hydroxyquinoline, which was filtered off. To the filtrate was added ethyl acetate and the mixture was washed once with a diluted aqueous hydrochloric acid solution and then twice with water. The mixture was concentrated and the residue formed was subjected to column chromatography to provide 15 g of an equivalent mixture of 2',6'-dimethoxyundecanophenone and 1,3-dimethoxy-2-(n-decyloxycarbonyl)benzene. The mixture was dissolved in a mixture of 50 ml of water and 100 ml of ethanol together with 10 g of potassium hydroxide. After refluxing the solution for 20 hours, the product was extracted with n-hexane. The extract was concentrated and the residue formed was subjected to column chromatography to provide 6.0 g of 2',6'-dimethoxyundecanophenone. Furthermore, 6 ml of boron tribromide was placed in a 100 ml three-neck flask together with 30 ml of methylene chloride. While stirring the mixture under ice-cooling, 30 ml of a methylene chloride solution of 6 g of 2',6'-dimethoxyundecanophenone was added dropwise to the mixture over a period of 15 minutes. Thereafter, the mixture was stirred for 1 hour at room temperature, poured in ice-water, and the product was extracted with ethyl acetate. After concentrating the extract, the residue formed was purified by column chromatography to provide 4.5 g of light yellow crystals having a melting point of 74.5°–75.5° C. The structure of the product was confirmed by mass spectrography, nuclear magnetic resonance spectra.

Elementary Analysis for $C_{17}H_{26}O_3$:

|  | C | H |
| --- | --- | --- |
| Calculated (%) | 73.34 | 9.41 |
| Found (%) | 73.17 | 9.56 |

SYNTHESIS EXAMPLE 2

Synthesis of Compound (3):

In a 100 ml three-neck flask was placed 50 ml of 2',6'-dihydroxyundecanophenone and after dissolving the undecanophenone in 50 ml of chloroform, the solution thus formed was stirred under ice-cooling. To the solution was added dropwise 10 ml of a chloroform solution of 1.4 ml of sulfuryl chloride over a period of 15 minutes. Thereafter, the mixture was stirred for 2 hours at room temperature and then after adding thereto n-hexane, the mixture was washed twice with water. After drying the reaction mixture with magnesium sulfate, the product was concentrated and the residue thus obtained was recrystallized from methanol to provide the light yellow crystals of 3'-chloro-2',6'-dihydroxyundecanophenone having a melting point of 76°–77° C. The structure was confirmed by carrying out analysis such as mass spectrography and nuclear magnetic resonance spectra.

Elementary Analysis for $C_{17}H_{25}ClO_3$:

|  | C | H | Cl |
| --- | --- | --- | --- |
| Calculated (%) | 65.27 | 8.06 | 11.33 |
| Found (%) | 65.18 | 8.01 | 11.54 |

SYNTHESIS EXAMPLE 3

Synthesis of Compound (4):

The same reaction procedure as in Synthesis Example 2 was followed except that 2.8 ml of sulfuryl chloride was used. By recrystallizing the product from methanol, light yellow crystals of the desired compound having a melting point of 82°–83° C. were obtained. The structure was confirmed by carrying out analysis such as mass spectrography and nuclear magnetic resonance spectra.

Elementary Analysis for $C_{17}H_{24}ClO_3$:

|  | C | H | Cl |
| --- | --- | --- | --- |
| Calculated (%) | 58.80 | 6.97 | 20.42 |
| Found (%) | 58.66 | 7.06 | 20.52 |

SYNTHESIS EXAMPLE 4

Synthesis of Compound (9):

In 400 ml of acetone were suspended 17.0 g of 2,6-dimethoxybenzenethiol, 25 g of n-dodecyl bromide, and 25 g of anhydrous potassium carbonate. After refluxing the suspension under a nitrogen atmosphere, the suspension was stirred for 6 hours. Insoluble matters were then filtered off and the filtrate was concentrated. The oily material thus obtained was purified by column chromatography (using silica gel as a carrier) using a solvent mixture of ethyl acetate and n-hexane to provide 24 g of an oily product.

The aforesaid product was dissolved in 100 ml of glacial acetic acid and after adding dropwise 25 ml of an aqueous 30% hydrogen peroxide solution to the solution at 70°–80° C., the mixture was stirred as it was for 4 hours.

The reaction mixture was poured into 500 ml of water, extracted with 150 ml of ethyl acetate, and the extract was sufficiently washed with water. After drying the extract with anhydrous sodium sulfate, the solvent was distilled off from the extract. The residue was purified by column chromatography using a mixed solvent of n-hexane and benzene to provide 15 g of an oily product.

Then, 15 g of the aforesaid oily product was dissolved in 300 ml of methylene dichloride. After cooling the solution to −10° C., 80 ml of methylene dichloride solution of 16 ml of boron tribromide were added. Then, after stirring the mixture for 5 hours at room temperature, the reaction mixture was poured in 500 ml of water. The organic layer thus formed was sufficiently washed until the pH of the washings became 6–7 and then dried by anhydrous magnesium sulfate. The solvent was distilled off and the residue thus formed was purified by column chromatography using a mixed solvent of ethyl acetate and benzene to provide 9 g of the light yellow crystals of the desired compound.

Elementary Analysis for $C_{18}H_{30}O_4S$:

|  | C | H | S |
|---|---|---|---|
| Calculated (%) | 63.12 | 8.83 | 9.36 |
| Found (%) | 63.09 | 8.90 | 9.47 |

SYNTHESIS EXAMPLE 5

Synthesis of Compound (13):

In 50 ml of water was dissolved 12.1 g of sodium 3,5-dimethoxybenzenesulfinate and after adding thereto a solution of 11.1 g of n-decyl bromide dissolved in 100 ml of tetrahydrofuran, the mixture was stirred for 5 hours at room temperature.

The reaction mixture was poured in 500 ml of water, extracted with 200 ml of ethyl acetate, and the extract was washed with water and then dried by anhydrous sodium sulfate. After sufficiently distilling off the solvent from the reaction mixture, the residue was dissolved in 200 ml of methylene chloride. The solution was cooled to a temperature of −10° C. to −5° C. Then, while maintaining the solution at the above temperature, 100 ml of a methylene chloride solution of 13 ml of boron tribromide was added dropwise to the solution over a period of 15 minutes and the resultant mixture was stirred for 6 hours at room temperature.

Then, the reaction mixture was poured into 1.0 l of water. After washing the methylene chloride solution with water until the pH thereof became 6–7, the solution was dried by anhydrous magnesium sulfate. The solvent was then distilled off from the solution.

The residue thus formed was recrystallized from a mixed solvent of n-hexane and benzene to provide 9.5 g of the light yellow crystals of the desired compound.

Elementary Analysis for $C_{16}H_{26}O_4S$:

|  | C | H | S |
|---|---|---|---|
| Calculated (%) | 61.12 | 8.34 | 10.20 |
| Found (%) | 61.26 | 8.42 | 10.09 |

The amount of coated silver in this invention differs according to the kind of the desired product but is generally in the range of from 0.1 g/m² to 6 g/m², preferably from 0.2 g/m² to 4 g/m².

The developing temperature in this invention is in a range of 10°–60° C., preferably a range of 20°–45° C. Also, the pH of the developer or activator used in this invention is in a range of about 9 to about 14, preferably in a range of 11–14.

The coating amount of the coupler in this invention is in a range of $2\times10^{-3}$ mole to $5\times10^{-1}$ mole, preferably $1\times10^{-2}$ mole to $5\times10^{-1}$ mole per mole of silver.

The coloring developing agent used in this invention is a color developing agent which forms a dye by causing an oxidative coupling with an active methylene compound. As such a color developing agent, an aromatic primary amine is preferred and further the p-phenylenediamines shown by the following general formula (IV) or the p-aminophenols shown by general formula (V) and the precursors of these compounds are more preferred:

(IV)

(V)

wherein R, $R_1$, $R_2$, $R_3$, $X_1$, and $X_2$ each represents a hydrogen atom, a halogen atom, an alkyl group, a substituted alkyl group (examples of the substituent are a haloalkyl group, a sulfoalkyl group, a carboxyalkyl group, an ethoxyalkyl group, a hydroxyalkyl group, an alkoxycarbonylalkyl group, an alkylsulfonamidoalkyl group, an alkylcarboxyamidoalkyl group, a cyanoalkyl group, etc.), an alkoxy group, an acetamido group, an aralkyl group, an alkylsulfonyl group, a carbamoyl group, or a sulfamoyl group and also $R_1$ and $R_2$ may combine with each other to form one ring.

It is preferred that the compounds shown by the foregoing formula form the salts thereof, such as the hydrochlorides, sulfates, sulfites, p-toluenesulfonates, oxalates, etc.

Practical examples of the preferred p-phenylenediamines are, for example, N,N-diethyl-p-phenylenediamine hydrochloride, 2-amino-5-diethylaminotoluene hydrochloride, 2-amino-5-(N-ethyl-N-laurylamino)toluene, 4-[N-ethyl-N-(β-hydroxyethyl)amino]aniline sulfate, 2-methyl-4-[N-ethyl-N-(β-hydroxyethyl)amino]aniline sulfate, N-ethyl-N-(β-methanesulfonamidoethyl)-3-methyl-4-aminoaniline sesquisulfate monohydrate described in U.S. Pat. No. 2,193,015, incorporated herein by reference, N-(2-amino-5-diethylaminophenylethyl)methanesulfonamide sulfate described in U.S. Pat. No. 2,592,364, incorporated herein by reference, and 4-amino-3-methyl-N-ethyl-N-methoxyethylaniline, 4-amino-3-methyl-N-ethyl-N-β-ethoxyethylaniline, and 4-amino-3-methyl-N-ethyl-N-β-butoxyethylaniline and the salts of them (e.g., sulfates, hydrochlorides, sulfites, p-toluenesulfates, etc.) described in U.S. Pat. Nos. 3,656,950, 3,698,525, all incorporated herein by reference.

Practical examples of the preferred p-aminophenols are p-aminophenol, 2,6-dibromo-4-aminophenol, 2,6-dichloro-4-aminophenol, 2-chloro-4-aminophenol, 2-fluoro-4-aminophenol, 3-fluoro-4-aminophenol, 2,6-dimethyl-4-aminophenol, 2-methyl-4-aminophenol, 3-methyl-4-aminophenol, 3-methoxy-4-aminophenol.

The image containing the dye formed by the oxidative coupling reaction of the coupler in this invention and the foregoing aromatic primary amine is a black image having almost no other color and the change in the chemical structure of the developing agent has almost no influence on the black hue of the image.

Examples of the precursors of these developing agents are Schiff base-type precursors as described in Japanese Patent Application (OPI) No. 9924/79 and U.S. Pat. No. 3,342,599; the water-soluble multivalent metal complexes of p-phenylenediamines as described in U.S. Pat. No. 3,719,492; the precursors formed by substituting the amino group of aromatic primary amine for a methanephosphonic acid described in U.S. Pat. No. 3,419,395; the phthalimide precursors described in British Pat. No. 1,069,051; the precursors having aryleothoxycarbonyl bonded to amino group as described in Japanese Patent Application (OPI) No. 135628/78; and the precursors obtained by the reaction of tetraaryl borates and aromatic primary amines described in Japanese Patent Application (OPI) No. 6235/81.

They can be used by a method of using a latex polymer as described in U.S. Pat. No. 3,518,088; a method of using the latex polymer described in *Research Disclosure*, 14850; or a method of using the cyclic β-dicarbonyl compound described in Japanese Patent Application (OPI) No. 111729/78.

The aromatic primary amine described above can be incorporated in a developer or a photographic material and the precursor thereof is mainly incorporated in a photographic material.

When the color developing agent or the precursor thereof is not incorporated in a photographic material, known developer components may be incorporated in the color developer together with the foregoing developing agent. For example, sodium hydroxide, potassium hydroxide, sodium carbonate, potassium carbonate, sodium tertiary phosphate, potassium tertiary phosphate, potassium metaborate, borax, etc., are used solely or a combination thereof as an alkali agent, buffer, etc. Also, for the purpose of giving a buffering faculty, for the convenience of preparing the developer, or for the purpose of increasing the ionic strength, various salts such as disodium hydrogenphosphate, dipotassium hydrogenphosphate, potassium dihydrogenphosphate, sodium dihydrogenphosphate, sodium hydrogencarbonate, potassium hydrogencarbonate, borates, an alkali nitrate, an alkali sulfate, etc., can be used.

The color developer used in this invention may, if necessary, contain a desired development accelerator. For example, there are, as such development accelerators, various kinds of pyridinium compounds and other cationic compounds described in U.S. Pat. No. 2,648,604, Japanese Patent Publication No. 9503/69, and U.S. Pat. No. 3,671,247; cationic dyes such as phenosafranine; neutral salts such as thallium nitrate and potassium nitrate; polyethylene glycol and the derivatives thereof described in Japanese Patent Publication No. 9504/69, and U.S. Pat. Nos. 2,533,990, 2,531,832, 2,950,970 and 2,577,127; nonionic compounds such as polythioethers; the organic solvents and organic amines described in Japanese Patent Publication No. 9509/69 and Belgian Patent No. 682,862; ethanolamine, ethylenediamine, diethanolamine, 2-(2-aminoethylamino)ethanol, and the accelerators described in L. F. A. Mason, *Photographic Processing Chemistry*, pages 40-43 (Focal Press, London, 1966).

Other examples of useful development accelerators are benzyl alcohol and phenyl ethyl alcohol described in U.S. Pat. No. 2,515,147 and pyridine, ammonia, hydrazine, and amines described in *Journal of the Society of Photographic Science and Technology of Japan*, Vol. 14, 74 (1952).

Also, sodium sulfite, potassium sulfite, potassium hydrogensulfite, or sodium hydrogensulfite which is usually used as preservatives may be added to the color developer.

The color developer used in this invention may further contain, if necessary, a desired anti-foggant. Useful anti-foggants include alkali metal halides such as potassium bromide, sodium bromide, potassium iodide, etc., and organic anti-foggants. Examples of organic anti-foggants include nitrogen-containing heterocyclic compounds such as benzotriazole, 6-nitrobenzimidazole, 5-nitroisoindazole, 5-methylbenzotriazole, 5-nitrobenzotriazole, 5-chlorobenzotriazole, etc.; mercapto-substituted heterocyclic compounds such as 1-phenyl-5-mercaptotetrazole, 2-mercaptobenzimidazole, 2-mercaptobenzothiazole, etc.; and mercapto-substituted aromatic compounds such as thiosalicylic acid. Particularly preferred organic anti-foggants are nitrogen-containing heterocyclic compounds and, in particular, nitrogen-containing heterocyclic compounds having no mercapto substituent. The addition amount of the anti-foggants is 1 mg to 5 g, preferably 5 mg to 1 g per liter of the color developer.

Furthermore, polyphosphoric acid compounds such as sodium hexametaphosphate, sodium tetrapolyphosphate, sodium tripolyphosphate, and the potassium salts of the above-described polyphosphoric acids; aminopolycarboxylic acids such as hydroxyalkanediphosphoric acid, ethylenediaminetetraacetic acid, nitrilotriacetic acid, cyclohexanediaminetetraacetic acid, iminodiacetic acid, N-hydroxymethylethylenediaminetriacetic acid, diethylenetriaminepentaacetic acid, etc., described in U.S. Pat. No. 1,420,656, or combinations of them may be used as a water softener. The addition amount depends on the hardness of water used but is usually about 0.5 to 1 g/l. Moreover, calcium or magnesium masking agents may be used in the photographic processing solutions. These materials are described in detail in J. Willems, *Belgische Chemische Industrie*, Vol. 21, 325 (1956) and ibid., Vol. 23, 1105 (1958).

In the case of reversal processing, a competing coupler, a fogging agent, and a complementary developing agent may be also incorporated in the color developer.

As the competing coupler, citrazinic acid, J-acid, H-acid, etc., are useful. Furthermore, the compounds described in, for example, U.S. Pat. No. 2,742,832, Japanese Patent Publication Nos. 9504/69, 9506/69 and 9507/69, and U.S. Pat. Nos. 3,520,690, 3,560,212, 3,645,737, etc., can be used as the competing coupler.

As the fogging agent, an alkali metal borohydride, amineborane, ethylenediamine, etc., can be used. The compounds described in Japanese Patent Publication No. 38816/72 are also useful as the fogging agent.

As the complementary developing agent, p-aminophenol, N-benzyl-p-aminophenol, 1-phenyl-3-pyrazolidone, etc., can be used. The compounds described in, for example, Japanese Patent Publication Nos. 41475/70 and 19037/71 and Japanese Patent Application (OPI) No. 9924/79 are useful as the complementary developing agent.

When a color developing agent is incorporated in the photographic material, the photographic material can be developed by a so-called activator solution composed of the components for the color developer excluding the color developing agent. In this case a complementary developing agent may be incorporated in the photographic material.

The couplers of this invention can be applied to radiographic materials, ordinary black and white negative photographic materials, photographic materials for printing, ordinary black and white photographic papers, positive photographic materials, reversal photographic materials, etc. The couplers of the present invention are most useful in connection with X-ray photographic materials and black and white negative photographic materials for picture taking. The images obtained may be composed of silver images and dye images superposed thereon or may be composed of the dye only formed by applying silver removing treatment.

Also, a method known as color intensification can be used in this invention. For example, there is a method of using hydrogen peroxide described in, e.g., West German Patent Application (OLS) Nos. 1,813,920, 1,950,102, 1,995,901, 1,961,029, 2,044,833, 2,044,993, 2,056,360, 2,056,359 and 2,121,091 and the color intensification using Co (III) complex described in U.S. Pat. Nos. 3,826,652, 3,834,907, 3,748,138 and 3,765,819.

For incorporating the coupler of this invention in a hydrophilic colloid constituting the photographic layer of the photographic material, a method of adding a color coupler to a hydrophilic colloid layer as an emulsion thereof can be employed. That is, according to the method as described in U.S. Pat. Nos. 2,322,027 and 2,304,939, the coupler is dissolved in an organic solvent, the solution is dispersed by emulsification in an aqueous medium using a surface active agent, and the emulsified dispersion is added to a photographic hydrophilic colloid. As the organic solvent used for the foregoing purpose, a high-boiling organic solvent having a boiling point of not lower than 175° C. and a low-boiling organic solvent having a boiling point of about 30° C. to about 150° C. may be used solely or as a mixture of a desired mixing ratio of them.

Examples of the foregoing high-boiling organic solvent used include di-n-butyl phthalate, benzyl phthalate, triphenyl phosphate, tri-o-cresyl phosphate, diphenyl-mono-p-tert-butylphenyl phosphate, monophenyl-di-p-tert-butylphenyl phosphate, diphenyl-mono-o-chlorophenyl phosphate, monophenyl-di-o-chlorophenyl phosphate, 2,4-di-n-amylphenol, 2,4-di-t-amylphenol, N,N-diethyllaurylamide, as well as trioctyl phosphate, trihexyl phosphate, tricyclohexyl phosphate, etc., as described in U.S. Pat. No. 3,676,137.

Also, a method of dispersing the coupler using the above-described latex and then adding the dispersion to the coating composition can be used.

Examples of the surface active agents used in the practice of this invention are nonionic surface active agents such as saponin (steroid series), alkylene oxide derivatives (e.g., polyethylene glycol, polyethylene glycol/polypropylene glycol condensation products, polyethylene glycol alkyl ethers, polyethylene glycol alkylaryl ethers, polyethylene glycol esters, polyethylene glycol sorbitan esters, polyalkylene glycol alkylamines, polyalkylene glycol alkylamides, silicone-ethylene oxide adduct, etc.), glycidol derivatives (e.g., polyglyceride alkylenesuccinate, alkylphenol polyglyceride, etc.), polyhydric alcohol fatty acid esters, sugar alkylesters, etc.; anionic surface active agents having an acid group such as carboxy group, sulfo group, phospho group, sulfuric acid ester group, phosphoric acid ester group, etc., such as alkylcarboxylates, alkylsulfonates, alkylbenzenesulfonates, alkylnaphthalenesulfonates, alkylsulfuric acid esters, alkylphosphoric acid esters, N-acyl-N-alkyltaurines, sulfosuccinic acid esters, sulfoalkyl polyoxyethylenealkylphenyl ethers, polyoxyethylenealkylphosphoric acid esters, etc.; amphoteric surface active agents such as aminoacids, aminoalkylsulfonic acids, aminoalkylsulfuric acid esters, aminoalkylphosphoric acid esters, alkylbetaines, amineoxides, etc.; and cationic surface active agents such as alkylamines, aliphatic or aromatic quaternary ammonium salts, heterocyclic quaternary ammonium salts such as pyridinium salts, imidazolium salts, etc., and phosphonium salts or sulfonium salts containing aliphatic or heterocyclic ring.

The silver halide emulsion is usually prepared by mixing an aqueous solution of a water-soluble silver salt (e.g., silver nitrate) and an aqueous solution of a water-soluble halide (e.g., potassium bromide) in the presence of a water-soluble polymer such as gelatin. Examples of useful silver halides include silver chloride, silver bromide as well as a mixed silver halides such as silver chlorobromide, silver iodobromide, silver chloroiodobromide, etc.

These silver halide grains may be a cubic system, an octahedron, a mixed crystal system.

Furthermore, two or more kinds of silver halide photographic emulsions prepared separately may be mixed to provide the silver halide photographic emulsion used in this invention. Still further, the crystal structure of the silver halide grains may be one having a uniform property throughout the whole grain, or may be a structure wherein the property of the inside differs from the property of the surface portion thereof, or may be a so-called conversion-type silver halide grain as described in, for example, British Pat. No. 635,841 and U.S. Pat. No. 3,622,318. Also, the silver halide grains may be of the type of mainly forming latent images on the surface or of the type of forming latent images in the inside thereof. These photographic emulsions are described in, for example, Mees, *The Theory of Photographic Process*, published by Macmillan Co., P. Glafkides, *Chimie Photographique*, published by Paul Montel (1957), etc., and can be prepared by a conventional ammonia method, neutral method, acid method, etc.

The foregoing silver halide emulsion can be chemically sensitized by an ordinary manner. As chemical sensitizers used in the purpose, there are gold compounds such as the chloroaurates, gold trichloride, etc., as described in U.S. Pat. Nos. 2,399,083, 2,540,085, 2,597,856 and 2,597,915; the salts of noble metals such as platinum, palladium, iridium, rhodium, ruthenium, etc., as described in U.S. Pat. Nos. 2,448,060, 2,540,086, 2,566,245, 2,566,263 and 2,598,079; the sulfur compounds forming silver sulfite by causing a reaction with silver salts as described in U.S. Pat. Nos. 1,574,944, 2,410,689, 3,189,458, 3,501,313, etc.; the stannous salts and amines as described in U.S. Pat. No. 2,487,850, 2,518,698, 2,521,925, 2,521,926, 2,694,637, 2,983,610, and 3,201,254; and other reducing materials.

It is sometimes preferred that the photographic materials of this invention contain various additives for obtaining desired development characteristics, imaging characteristics, film properties, etc. Examples of such additives include organic compounds having an iodide of a salt form or a mercapto free radical, such as, for example, phenylmercaptotetrazole, alkali metal iodides. However, it is desirable to avoid the use of a large amount of such an additive.

As other additives which may be incorporated in the photographic elements, there are hardening agents, plasticizers, wetting agents, surface improving agents, brighteners, etc., and other additives known in the field of photography.

Examples of the hardening agents are aldehydes and blocked aldehydes described in U.S. Pat. No. 3,237,264 and the ketones, carboxylic acid derivatives, sulfonate esters, halogenated sulfonyl ethers, vinylsulfonyl ethers, activated halogen compounds, and epoxy compounds described in U.S. Pat. No. 3,539,644.

Examples of the hydrophilic colloid used in this invention are gelatin; colloidal albumin; casein; cellulose derivatives such as carboxymethyl cellulose, hydroxyethyl cellulose, etc.; sugar derivatives such as agar agar, sodium alginate, starch derivatives, etc.; synthetic hydrophilic colloids such as polyvinyl alcohol, poly-N-vinylpyrrolidone, polyacrylic acid copolymer, polyacrylamide, derivatives of them, and partially hydrolyzed products of them. If necessary, a mixture of two or more these colloids which are compatible with each other can be used. In the above-described hydrophilic colloids, gelatin is most generally used but gelatin may be partially or wholly replaced with a synthetic polymer or a so-called gelatin derivative may be used in place of gelatin.

The silver halide photographic emulsions used in this invention may be spectrally sensitized or supersensitized by cyanine dyes such as cyanine, merocyanine, carbocyanine, etc., solely or as a combination of them. These dye sensitizations are known and are described in, for example, U.S. Pat. Nos. 2,493,748, 2,519,001, 2,977,229, 3,480,434, 3,672,897, 3,703,377, 2,688,545, 2,912,329, 3,397,060, 3,615,635, and 3,628,964, British Pat. Nos. 1,195,302, 1,242,588 and 1,293,862, West German Patent Application (OLS) Nos. 2,030,326 and 2,121,780, Japanese Patent Publication Nos. 4936/68, 14030/69 and 10773/68, U.S. Pat. Nos. 3,511,664, 3,522,052, 3,527,641, 3,615,613, 3,615,632, 3,617,295, 3,635,721 and 3,694,217, and British Pat. Nos. 1,137,580 and 1,216,203. They are properly selected according to the wavelength region, sensitivity, etc., to be sensitized, and the purpose of the photographic materials.

Useful supports for the photographic materials of this invention include cellulose nitrate films, cellulose acetate films, cellulose acetate butyrate films, cellulose acetate propionate films, polystyrene films, polyethylene terephthalate films, polycarbonate films, the laminates of these films, thin glass sheets, papers, etc., which are usually used for photographic materials. Furthermore, baryta-coated papers or papers coated or laminated with an α-olefin polymer, in particular, a polymer of an α-olefin having 2 to 10 carbon atoms, such as polyethylene, polypropylene, ethylenebutene copolymer, etc., or plastic films having matted surfaces for improving the adhesion with other polymers as disclosed in Japanese Patent Publication No. 19068/72.

A transparent support or an opaque support is selected according to the kind and purpose of the photographic material. When using a transparent support, the support may be colorless or may be colored by the addition of dyes or pigments. Such a colored transparent support is conventionally known in X-ray films, etc., and also by J. SMPTE, 67, 296 (1958).

Examples of opaque supports include papers which are originally opaque as well as opaque films prepared by adding a dye or pigment such as titanium oxide into transparent films, plastic films surface-treated by the method shown in Japanese Patent Publication No. 19068/72, papers or plastic films imparted with a complete light-shading property by adding thereto carbon black, dyes, etc. If necessary, a layer having good adhesion with the support and the silver halide photographic emulsion layer is formed on the support as a subbing layer. Also, the support may be subjected to a pre-treatment such as corona discharging, ultraviolet irradiation, flame treatment, etc., for further improving the adhesion with the photographic emulsion layer.

The photographic layers practically used in this invention may be formed by using a dip coating method, an air knife coating method, a curtain coating method, or a coating method using the hopper as described in U.S. Pat. No. 2,681,294.

The invention will be further explained by the following examples.

EXAMPLE 1

Several of the couplers of this invention as illustrated above or the known coupler illustrated below were coated on a support by the manner described below and the properties were compared.

Comparison Coupler A:

Comparison Coupler B:

A mixture of $1.7 \times 10^{-2}$ mole of the resorcinol coupler shown in Table 1, 7.5 g of tricyclohexyl phosphate, and 5 ml of ethyl acetate was heated to 60° C. to dissolve the coupler. Then, 2.5 ml of a 5 wt% sodium dodecylbenzenesulfonate was added to 30 g of a 10 wt% inert gelatin solution and the coupler solution prepared above was added to the gelatin solution and dispersed therein by emulsification.

To the emulsion thus prepared was added 100 g of a gelatino silver iodobromide emulsion (1.5% silver iodide, and 50 g/mole-Ag of gelatin) and 10 ml of 2 wt% bis(vinylsulfonylmethyl)ether to provide a coating solution.

The coating solution was coated on a blue-dyed polyethylene terephthalate film at a silver coverage of 2 g/m² and a gelatin protective layer was formed thereon at a gelatin coverage of 2 g/m².

Various photographic materials containing various kinds of resorcinol couplers were prepared and each of the photographic materials was image-exposed and processed by the following manners using a roller conveyer-type processor.

|  | Processing Temperature | Processing Time |
|---|---|---|
| Development | 35° C. | 25 sec |
| Fix | 34° C. | 25 sec |
| Wash | 33° C. | 25 sec |
| Drying | 50° C. | 15 sec |

The compositions of the developer and the fix solution used in the above processing steps were as follows:

| Developer: | |
|---|---|
| Water | 900 ml |
| Anhydrous sodium sulfite | 4 g |
| Sodium carbonate monohydrate | 20 g |
| Sodium bromide | 2 g |
| N,N—Diethyl-p-phenylenediamine hydrochloride | 3 g |
| 1-Phenyl-4-methyl-4-hydroxymethyl-3-pyrazolidone | 0.1 g |
| pH adjusted to 13.0 at 20° C. | |
| Water to make | 1,000 ml |
| Fix Solution: | |
| Water | 500 ml |
| Ammonium thiosulfate | 200.0 g |
| Anhydrous sodium sulfite | 20.0 g |
| Boric acid | 8.0 g |
| Disodium ethylenediaminetetraacetate | 0.1 g |
| Aluminum sulfate | 15.0 g |
| Sulfuric acid | 2.0 g |
| Glacial acetic acid | 22.0 g |
| Water to make | 1,000 ml |
| The pH value of the fix solution was about 4.10 at 20° C. | |

The process used was an automatic processor for X-ray films ("Fuji RN", trade name, made by Fuji Photo Film Co., Ltd.) and the total processing time was 90 seconds.

The measurement results of the photographic images thus formed are shown in the following table.

Each of the sample films thus processed as described above was further subjected to the following processings to provide the bleached film having only a dye image.

|  | Processing Temperature | Processing Time |
|---|---|---|
| Bleach | 35° C. | 3 min |
| Wash | 33° C. | 25 sec |
| Fix | 34° C. | 25 sec |
| Wash | 33° C. | 25 sec |
| Drying | 50° C. | 30 min |

The composition of the bleach solution was as follows and that of the fix solution was the same as described above.

| Bleach Solution: | |
|---|---|
| Water | 800 ml |
| Ethylenediaminetetraacetic acid iron (III) sodium.2H₂O | 100 g |
| Potassium bromide | 50 g |
| Ammonium nitrate | 50 g |
| Boric acid | 5 g |
| The pH of the solution was adjusted to 5.0 with aqueous ammonia at 20° C. | |
| Water to make | 1,000 ml |

The properties of the dye images thus formed were measured and also shown in Table 1.

TABLE 1

| Test No. | Coupler | Before Bleaching | | | After Bleaching | | |
|---|---|---|---|---|---|---|---|
| | | Fog* | Dm* | Hue | Fog* | Dm* | Hue |
| 1 | None | 0.14 | 0.40 | Black | 0.11 | 0.12 | Colorless |
| 2 | Compound 2 | 0.17 | 1.94 | Black | 0.16 | 1.43 | Black |
| 3 | Compound 3 | 0.20 | 2.47 | Black | 0.18 | 1.97 | Black |
| 4 | Compound 7 | 0.16 | 1.75 | Black | 0.14 | 1.22 | Black |
| 5 | Compound 9 | 0.16 | 1.81 | Black | 0.15 | 1.30 | Black |
| 6 | Compound 11 | 0.19 | 2.19 | Black | 0.18 | 1.66 | Black |
| 7 | Compound 14 | 0.15 | 1.73 | Black | 0.14 | 1.22 | Black |
| 8 | Comparison Coupler A** | 0.16 | 1.62 | Red Black | 0.15 | 1.16 | Red Purple |
| 9 | Comparison Coupler B** | 0.18 | 1.93 | Yellow Brown | 0.10 | 0.55 | Yellow Brown |

*The measured density is visual density.
**Comparison couplers are black coloring couplers described in Japanese Patent Application (OPI) No. 9924/79.

Since the Dm after bleaching is the density of the dye only, as the density is higher and the color is more black, the amount of coating silver can be more reduced. The densities of the dyes in Test Nos. 2–7 of this invention are higher than those of Comparison Test Nos. 8 and 9 and also the hues of the former samples are nearer black than those of the latter samples. In particular, it is understood that the color densities of Test Nos. 2, 3, and 6 of this invention are about 1.5 times those of the compassion samples.

Figure 1:
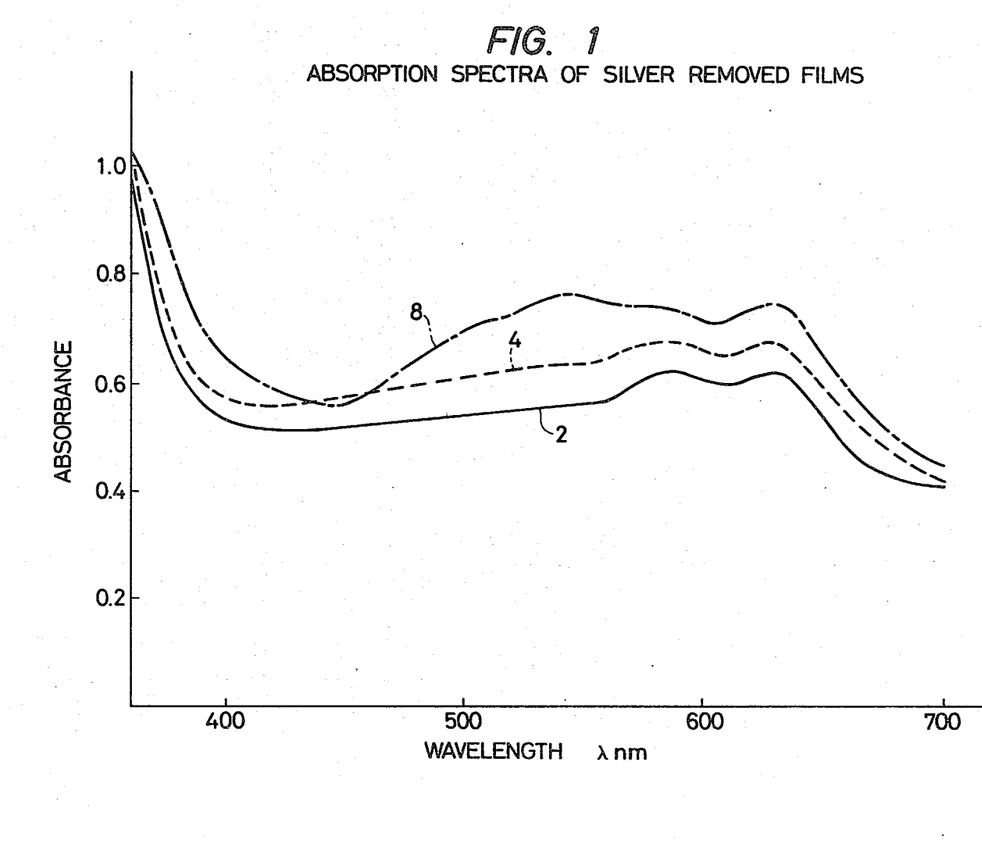
FIG. 1 is a graph showing the absorption spectra in the visible region of the films of test Nos. 2, 4 and 8 obtained in Example 1 after being subjected to a bleaching (silver removing) treatment.

The spectral absorption curves in visible region of the films after bleaching obtained in the above experiments are shown in FIG. 1.

As understood from FIG. 1, in the sample of Comparison Test No. 8, the absorbance at about 440 nm is low and the color is generally reddish. On the other hand, it is understood that the samples of Test Nos. 2 and 4 of this invention show relatively flat absorptions and the color is black. However, since the absolute values of the absorbances were measured at proper density portions which were liable to be compared, it was impossible to compare the samples with each other.

EXAMPLE 2

To the coating solution having the same composition as in Example 1 were added 5 g of N,N-diethyl-3-methyl-p-phenylenediamine hydrochloride, 6.7 g of nickel nitrate hexahydrate and 5.1 g of 4,4-dihydroxymethyl-3-pyrazolidone per 100 g of the base emulsion, and they were dissolved therein.

The coating composition was coated on a blue-dyed polyethylene terephthalate film at a silver coverage of 2 g/m$^2$ and further a gelatin solution was coated on the layer at a gelatin coverage of 2 g/m$^2$ to form a protective layer.

Various photographic materials containing various kinds of the resorcinol couplers and the foregoing color developing agent were prepared and each of the photographic materials were image-exposed and subjected to the following processings.

|  | Processing Temperature | Processing Time |
|---|---|---|
| Activator | 25° C. | 25 sec |
| Fix | 25° C. | 25 sec |
| Wash | 25° C. | 25 sec |
| Drying | 50° C. | 15 min |

The composition of the activator used in the above process was as follows and the composition of the fix solution was the same as that in Example 1.

| Activator Solution: | |
|---|---|
| Water | 900 ml |
| Sodium hydroxide | 12 g |
| Sodium bromide | 2 g |
| Benzyl alcohol | 10 ml |
| 2-(2-Aminoethylamino)ethanol | 5 ml |
| Water to make | 1,000 ml |

The measurement results of the photographic images thus formed are shown in the following table.

TABLE 2

| Test No. | Coupler | Fog | Dm | Hue |
|---|---|---|---|---|
| 16 | None | 0.24 | 0.60 | Black |
| 17 | Compound 2 | 0.29 | 2.28 | Black |
| 18 | Compound 9 | 0.27 | 2.05 | Black |
| 19 | Compound 3 | 0.28 | 2.51 | Black |
| 20 | Comparison Coupler A | 0.27 | 1.95 | Red Black |

As is clear from Table 2, when incorporating the color developing agent in the photographic materials, the couplers of this invention result in a more complete black and a higher Dm than those of the comparison sample.

EXAMPLE 3

Each of the photographic materials prepared by the same manner as in Example 2 was subjected to the following intensification treatment.

|  | Processing Temperature | Processing Time |
|---|---|---|
| Activator intensification | 40° C. | 25 sec |
| Fix | 40° C. | 25 sec |
| Wash | 35° C. | 25 sec |
| Drying | 50° C. | 15 min |

The composition of the activator intensifier was as follows:

| Activator Intensifier: | |
|---|---|
| Water | 900 ml |
| Benzyl alcohol | 10 ml |
| Co[(NH$_3$)$_6$]Cl$_3$ | 5 g |
| Na$_2$CO$_3$.H$_2$O | 10 g |
| Potassium bromide | 2 g |
| Hydroxyethanediphosphonic acid (50%) | 20 ml |
| pH adjusted to 12.5 | |
| Water to make | 1,000 ml |

The measurement results of the photographic images thus formed are shown in the following table.

TABLE 3

| Test No. | Coupler | Fog | Dm | Hue |
|---|---|---|---|---|
| 21 | None | 0.28 | 0.47 | Black |
| 22 | Compound 2 | 0.36 | 2.71 | Black |
| 23 | Compound 9 | 0.37 | 2.59 | Black |
| 24 | Compound 3 | 0.35 | 2.93 | Black |
| 25 | Comparison Coupler A | 0.37 | 2.31 | Red Black |

As is clear from the above results, when incorporating the color developing agent in the photographic materials, the couplers of this invention gave a more complete black and a higher Dm than those of the comparison sample, and the excellence of this invention was confirmed on the samples subjected to the intensification treatment.

While the invention has been described in detail and with reference to specific embodiments thereof, it will be apparent to one skilled in the art that various changes and modifications can be made therein without departing from the spirit and scope thereof.

What is claimed is:

1. A process for forming black and white images which comprises color developing with an aromatic primary amine a black and white photographic material comprising a support having formed thereon a silver halide photographic emulsion layer containing a black image-forming coupler represented by general formula (I) or (II):

(I)

(II)

wherein R represents wherein Y$_1$ represents an aliphatic group, an aryl group, an aralkyl group, or a heterocyclic group, said group preventing said coupler from diffusing from the emulsion layer containing it and X$_1$ and X$_2$ each represents a hydrogen atom or a coupling-off group capable of being released upon oxidative coupling reaction with a developing agent.

2. A process as claimed in claim 1, wherein R represents where $Y_1$ has the same meaning as defined above.

3. A process as claimed in claim 1, wherein Y represents an unsubstituted alkyl group or substituted alkyl group having 1 to 22 carbon atoms, an unsubstituted or substituted alkenyl group having 2 to 22 carbon atoms, an unsubstituted or substituted aralkyl group having 7 to 22 carbon atoms, an unsubstituted or substituted aryl group having 6 to 22 carbon atoms, an unsubstituted or substituted cycloalkyl group having 5 to 22 carbon atoms or an unsubstituted or substituted heterocyclic group having 5 to 22 carbon atoms.

4. A process as claimed in claim 1, wherein $X_1$ and $X_2$ each represents a hydrogen atom, a halogen atom, an unsubstituted or substituted alkoxy group, an aryloxy group, an alkylthio group, an arylthio group, an acyloxy group, a sulfonyloxy group, an acylamino group, a sulfonylamino group, an alkyloxycarbonyloxy group, an aryloxycarbonyloxy group or an imido group.

5. A process as claimed in claim 1, wherein R is attached to the 2-position of the resorcinol nucleus.

6. A process as claimed in claim 1, wherein silver is present in an amount of about 0.1 g/m² to 6 g/m².

7. A process as claimed in claim 2, wherein silver is present in an amount of about 0.2 g/m² to 4 g/m².

8. A process as claimed in any of claims 1, 2, or 3, wherein the coupler is present in an amount of about $2 \times 10^{-3}$ mole to $5 \times 10^{-1}$ mole per mole of silver.

9. A process as claimed in claim 8, wherein the coupler is present in an amount of about $1 \times 10^{-2}$ mole to $5 \times 10^{-1}$ mole per mole of silver.

10. A process as claimed in claim 1, wherein said aromatic primary amine is the compound represented by general formula (IV) or (V):

(IV)

-continued (V)

wherein R, $R_1$, $R_2$, $R_3$, $X_1$, and $X_2$ each represent a hydrogen atom, a halogen atom, an alkyl group, a substituted alkyl group, an alkoxy group, an acetamido group, an aralkyl group, an alkylsulfonyl group, a carbamoyl group, or a sulfamoyl group and $R_1$ and $R_2$ may combine with each other to form one ring.

11. A process as claimed in claim 10, wherein R represents where $Y_1$ has the same meaning as defined above.

12. A process as claimed in claim 10, wherein Y represents an unsubstituted alkyl group or substituted alkyl group having 1 to 22 carbon atoms, an unsubstituted or substituted alkenyl group having 2 to 22 carbon atoms, an unsubstituted or substituted aralkyl group having 7 to 22 carbon atoms, an unsubstituted or substituted aryl group having 6 to 22 carbon atoms, an unsubstituted or substituted cyclo-alkyl group having 5 to 22 carbon atoms or an unsubstituted or substituted heterocylic group having 5 to 22 carbon atoms.

13. A process as claimed in claim 10, wherein $X_1$ and $X_2$ each represents a hydrogen atom, a halogen atom, an unsubstituted or substituted alkoxy group, an aryloxy group, an alkylthio group, an arylthio group, an acyloxy group, a sulfonyloxy group, an acylamino group, a sulfonylamino group, an alkyloxycarbonyloxy group, an aryloxycarbonyloxy group or an imido group.

14. A process as claimed in claim 10, wherein R is attached to the 2-position of the resorcinol nucleus.

15. A process as claimed in claim 10, wherein silver is present in an amount of about 0.1 g/m² to 6 g/m².

16. A process as claimed in claim 11, wherein silver is present in an amount of about 0.2 g/m² to 4 g/m².

17. A process as claimed in claim 10, 11 or 12, wherein the coupler is present in amount of about $2 \times 10^{-3}$ mole to $5 \times 10^{-1}$ mole per mole of silver.

18. A process as claimed in claim 17, wherein the coupler is present in an amount of about $1 \times 10^{-2}$ mole to $5 \times 10^{1}$ mole per mole of silver.

* * * * *